United States Patent [19]

McDonald et al.

[11] Patent Number: 4,898,968
[45] Date of Patent: Feb. 6, 1990

[54] CYCLOPROPANE DERIVATIVES

[75] Inventors: Edward McDonald, Marlow; Roger Salmon, Bracknell, both of England

[73] Assignee: Imperial Chemical Industries PLC, London, England

[21] Appl. No.: 188,850

[22] Filed: May 2, 1988

Related U.S. Application Data

[62] Division of Ser. No. 928,461, Nov. 10, 1986, Pat. No. 4,760,443, which is a division of Ser. No. 712,252, Mar. 15, 1985, Pat. No. 4,661,488.

[30] Foreign Application Priority Data

Mar. 26, 1984 [GB] United Kingdom ............... 8407810
Jul. 20, 1984 [GB] United Kingdom ............... 8418612
Feb. 4, 1985 [GB] United Kingdom ............... 8502778

[51] Int. Cl.$^4$ ............................................. C07C 69/743
[52] U.S. Cl. ..................................................... 560/124
[58] Field of Search ......................................... 560/124

[56] References Cited

U.S. PATENT DOCUMENTS

| | | | |
|---|---|---|---|
| 3,818,009 | 6/1974 | Taylor et al. | 544/335 |
| 4,014,918 | 3/1977 | Martel | 560/124 |
| 4,048,215 | 9/1977 | Krief et al. | 560/124 |
| 4,379,930 | 4/1983 | Pews | 544/298 |
| 4,474,958 | 10/1984 | Reifschneider | 544/334 |
| 4,622,337 | 11/1986 | Elliott et al. | 560/124 |

FOREIGN PATENT DOCUMENTS

| | | | |
|---|---|---|---|
| 0097451 | 4/1984 | European Pat. Off. | 544/334 |
| 0105006 | 4/1984 | European Pat. Off. | 546/339 |

OTHER PUBLICATIONS

Chemical Abstracts, vol. 44, Abstract No. 1516e, Jan. 10, 1950.
Chemical Abstracts, vol. 96, Abstract No. 6245n, Jan. 4, 1982.
Chemical Abstracts, vol. 83(5), Abstract No. 42517t, Aug. 4, 1975.
Chemical Abstracts, vol. 90(9), Abstract No. 72140b, Feb. 26, 1979.

*Primary Examiner*—Richard A. Schwartz
*Assistant Examiner*—Zinna Northington-Davis
*Attorney, Agent, or Firm*—Cushman, Darby & Cushman

[57] ABSTRACT

Compounds of the formula

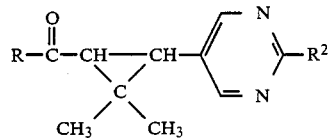

wherein $R^2$ represents an α-branched alkyl group containing from 3 to 6 carbon atoms, and R represents either (a) hydroxy, halo or alkoxy of up to six carbon atoms, or (b) the group —$OR^1$ where $R^1$ is the residue of an alcohol of formula $R^1OH$ which forms an insecticidal ester with chrysanthemic acid, permethrin acid or cyhalothrin acid. Methods for using these compounds to combat insect and acarine pests, as well as novel intermediates, are also disclosed.

2 Claims, No Drawings

CYCLOPROPANE DERIVATIVES

This is a division of application Ser. No. 928,461, filed Nov. 10, 1986, now U.S. Pat. No. 4,760,143, which is a division of Ser. No. 712,252, filed Mar. 15, 1985, now U.S. Pat. No. 4,661,488.

This invention relates to novel cyclopropane acids and derivatives thereof useful as intermediates, and to insecticidally active esters of these acids and compositions comprising them. The invention also relates to processes for preparing the novel acids and derivating and to novel compounds useful in such processes.

In a first aspect this invention provides novel cyclopropane compounds of formula I:

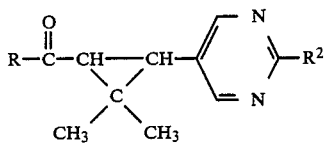

wherein $R^2$ represents an α-branched alkyl group, preferably containing from 3 to 6 carbon atoms, and either (a) R represents hydroxy, halo (especially chloro) or alkoxy of up to 6 carbon atoms, wherein such compounds are useful as intermediates for insecticides, or (b) R represents the group —$OR^1$ where $R^1$ is the residue of an alcohol of formula $R^1OH$ which forms an insecticidal ester when combined with chrysanthemic acid or permethrin acid or cyhalothrin acid. Permethrin acid is 3-(2,2-dichlorovinyl)-2,2-dimethylcyclopropane carboxylic acid and cyhalothrin acid is 3-(2-chloro-3,3,3-trifluoroprop-1-en-1-yl)-2,2-dimethylcyclopropane carboxylic acid.

More particularly R represents a group of the following general formula:

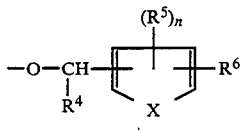

wherein X is oxygen, sulphur, vinylene or a group of formula —$CR^5$=Y— where Y is nitrogen or $CR^5$, $R^4$ is hydrogen, methyl, cyano or ethynyl, each $R^5$ is selected from hydrogen, halogen, and alkyl of up to 4 carbon atoms optionally substituted with halogen, and $R^6$ is hydrogen, halogen, alkyl of up to 4 carbon atoms, alkenyl of up to 6 carbon atoms, phenyl, phenoxy or benzyl, or phenyl, phenoxy or benzyl substituted with halogen or alkyl.

It will be appreciated that the compounds of formula I are capable of existing in different isomeric forms and as mixtures of isomers. Thus there are cis and trans isomers arising from the substitution pattern on the cyclopropane group and optical isomerism arises from the presence of the two chiral centres in the cyclopropane group leading to the possibility of (+)-cis, (−)-cis, (+)-trans and (−)-trans isomers. Further isomerism may be present in the insecticidally active esters of the invention if the alcohol moiety contains an alkenyl group or one or more chiral centres. All such individual isomeric forms and mixtures thereof, including racemates, are within the scope of the invention.

Specific compounds according to formula I useful as intermediates wherein R represents an alkoxy group of up to 6 carbon atoms include the methyl, ethyl, propyl and butyl esters of the acids of formula I wherein $R_3$ is one of (prop-2-yl, but-2-yl, pent-2-yl, pent-3-yl, 2-methylprop-2-yl, 2-methylbut-2-yl, cyclopropyl, and cyclohexyl.)

Particularly preferred compounds include:
ethyl (±)-trans-b 2,2-dimethyl-3-(2-prop-2-ylpyrimidn-5-yl)cyclopropane carboxylate,
ethyl (±)-trans-2,2-dimethyl-3-[2-(2-methylprop-2-yl)pyrimidin-5-yl]-cyclopropane carboxylate,
and the corresponding methyl and 2-methylprop-2-yl-esters.

The compounds of formula I wherein R is alkoxy of up to 6 carbon atoms may be prepared from the appropriately substituted 5-bromopyrimidine by the following reaction sequence:

(a) A 2-α-branched alkyl-5-bromopyrimidine is converted to the corresponding 5-formyl derivative by formation of a Grignard product, followed by treatment with dimethylformamide, thus:

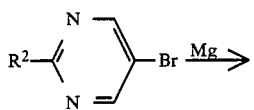

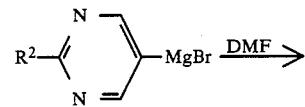

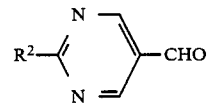

(b) The 5-formylpyrimidine is reacted with an O,O-dialkyl alkoxycarbonylmethylphosphonate in the presence of a base such as sodium hydride to give a 3-(pyrimidin-5-yl)propenoate, thus:

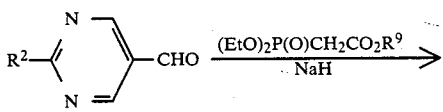

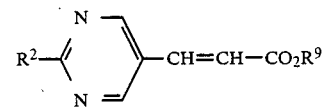

(c) The pyrimidinylpropenoate is reacted with an isopropyl triphenyl phosphonium salt in the presence of an organo metallic reagent such as n-butyllithium to give the cyclopropane ester, thus:

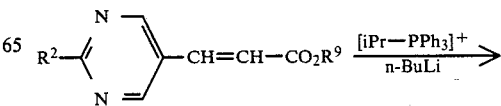

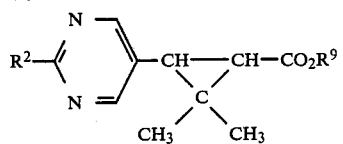

In an alternative procedure for preparing the 3-pyrimidin-5-yl-propenoates a 5-bromopyrimidine may be reacted directly with an alkyl propenoate (especially 1,1-dimethylethyl-propenoate) in the presence of a palladium II salt (eg. palladium II acetate), tetramethyl ethylene diamine and, preferably, a phosphine derivative (eg. triphenyl phosphine), thus:

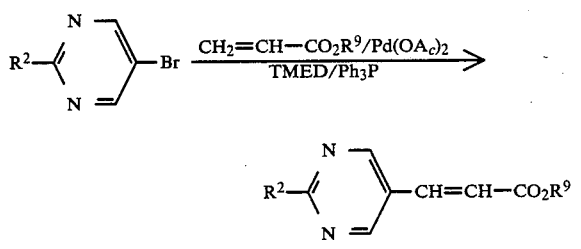

Some of the 5-bromopyrimidines used as starting materials in this sequence are novel. They can be prepared by reaction of a mucobromic acid derivative with an appropriate amidine, followed by decarboxylation of the pyrimidine carboxylic acid thus:

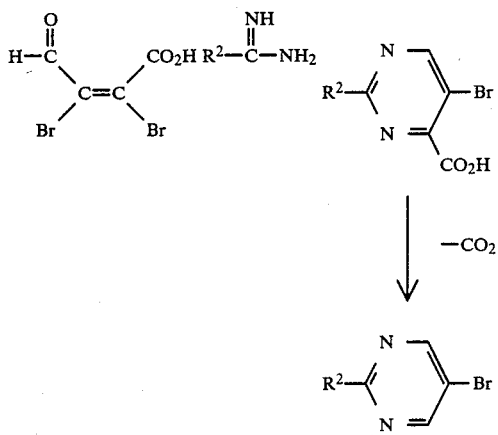

An alternative procedure for preparing the compounds of Formula I wherein R is alkoxy of up to 6 carbon atoms, and $R^2$ is a defined hereinabove employs the following reaction sequence:

(a) The ylid obtained by treating a phosphonium salt of formula:

$$[R^7O—CH_2—P(R^8)_3]^+ Y^-$$

wherein $Y^-$ is any suitable anion, eg. the chloride or bromide ion, and $R^7$ and $R^8$ are alkyl or aryl groups, preferably $R^7$ is alkyl of up to 6 carbon atoms such as methyl or ethyl and $R^8$ is phenyl, with a strong base in an aprotic solvent preferably dimsyl sodium in dimethyl sulphoxide (obtained by reaction of sodium hydride with dimethyl sulphoxide), is reacted with a compound of formula:

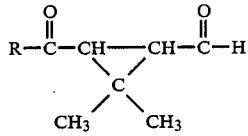

to obtain a compound of formula III

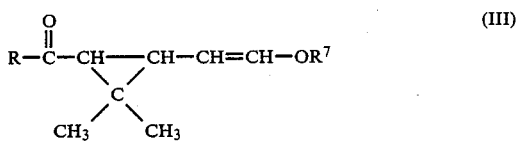

(b) The compound of formula III is treated with phosphoryl chloride and dimethylformamide under the conditions of the Vilsmeier-Haack reaction to obtain a compound of formula IV and/or a compound of formula V

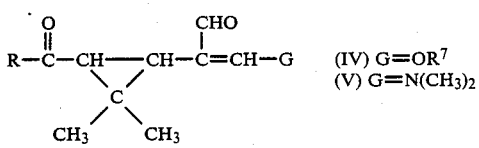

(c) Compound IV and/or compound V is reacted with an amidine of formula:

preferably in the presence of a base such as sodium methoxide in methanol to provide the compound of formula I wherein R is alkoxy as defined above.

The compounds of formulae III, IV and V have not previously been described. Accordingly a further aspect the present invention provides compounds of formula III, IV and V are hereinbefore defined useful as intermediates for the production of compounds of formula I.

Preferred compounds of formula III include the (±)-cis and (±)-trans isomers of the compounds where R is methoxy or ethoxy and $R^7$ is alkyl of up to 6 carbon atoms including the following:

methyl (±)-trans-3-[(E,Z)-2-methoxyvinyl]-2,2-dimethylcyclopropane carboxylate methyl (±)-cis-3-[(E,Z)-2-methoxyvinyl]-2,2-dimethylcyclopropane carboxylate ethyl (±)-trans-3-[(E,Z)-2-methoxyvinyl]-2,2-dimethylcyclopropane carboxylate ethyl (±)-cis-3-[(E,Z)-2-methoxyvinyl]-2,2-dimethylcyclopropane carboxylate The corresponding compounds of formula IV and formula V are also preferred, including the following:

methyl (±)-trans-3-[(E,Z)-1-formyl-2-methoxyvinyl]-2,2-dimethylcyclopropane carboxylate methyl (±)-cis-3-[(E,Z)-1-formyl-2-methoxyvinyl]-2,2-dimethylcyclopropane carboxylate methyl (±)-trans-3-[(E,Z)-2-dimethylamino-1-formylvinyl]-2,2-dimethylcyclopropane carboxylate methyl (±)-cis-3-[(E,Z)-2-dimethylamino-1-formylvinyl]-2,2-dimethylcyclopropane carboxylate together with the corresponding ethyl esters.

Further details of all these processes are set forth hereinafter in the Examples. The compounds of formula I wherein R represents hydroxy may be obtained by hydrolysis of the alkyl esters, preferably by alkaline hydrolysis using eg. aqueous alcoholic sodium hydroxide, and may be used directly in the synthesis of insecticidally useful esters or may be first converted to the compounds of formula I wherein R represents halo, preferably chloro, the reaction with a suitable halogenating agent such as thionyl chloride. Specific insecticidally useful compounds according to the invention include the esters derived from each of:

4-methyl-2,3,5,6-tetrafluorobenzyl alcohol
pentafluorobenzyl alcohol
4-allyl-2,3,5,6-tetrafluorobenzyl alcohol
4-methoxymethyl-2,3,5,6-tetrafluorobenzyl alcohol
3-phenoxybenzyl alcohol
α-cyano-3-phenoxybenzyl alcohol
6-phenoxypyrid-2-ylmethanol
1-cyano-1-(6-phenoxypyrid-2-yl)methanol
3-(4-chlorophenoxybenzyl) alcohol
α-ethynyl-3-phenoxybenzyl alcohols
1-(6-phenoxypyrid-2-yl)ethanol
4-fluoro-3-phenoxybenzyl alcohol
α-cyano-4-fluoro-3-phenoxybenzyl alcohol
5-benzyl-3-furylmethanol
2-allyl-3-methyl-4-hydroxycyclopent-2-enone
2-methyl-3-phenylbenzyl alcohol
including, where appropriate, single isomers and racemates thereof, and each of the acids of formula I (in the form of the racemic mixture of the trans isomers), or a single isomer thereof, wherein R² is one of prop-2-yl, but-2-yl, pent-2-yl, pent-3-yl, 2-methylprop-2-yl, 2-methylbut-2-yl, cyclopropyl and cyclohexyl.

Particularly preferred compounds include:
4-methyl-2,3,5,6-tetrafluorobenzyl (±)-trans-2,2-dimethyl-3-[2-(2-methylprop-2-yl)pyrimidin-5-yl]cyclopropane carboxylate (hereinafter "Compound I").
4-allyl-2,3,5,6-tetrafluorobenzyl (±)-trans-2,2-dimethyl-3-[2-(2-methylprop-2-yl)pyrimidin-5-yl]cyclopropane carboxylate (hereinafter "Compound II").
3-phenoxybenzyl (±)-trans-2,2-dimethyl-3-[2-(2-methylprop-2-yl)pyrimidin-5-yl]cyclopropane carboxylate (hereinafter "Compound III").
(±)-α-cyano-3-phenoxybenzyl (±)-trans-2,2-dimethyl-3-[2-(2-methylprop-2-yl)pyrimidin-5-yl]cyclopropane carboxylate (hereinafter "Compound IV").
6-phenoxypyrid-2-ylmethyl (±)-trans-2,2-dimethyl-3-[2-(2-methylprop-2-yl)pyrimidin-5-yl]cyclopropane carboxylate (hereinafter "Compound V").
(±)-1-cyano-1-(6-phenoxypyrid-2-yl)methyl (±)-trans-2,2-dimethyl-3-[2-(2-methylprop-2-yl)pyrimidin-5-yl]cyclopropane carboxylate (hereinafter "Compound VI").
2-methyl-3-phenylbenzyl (±)-trans-2,2-dimethyl-3[2-methylprop-2-yl)pyrimidin-5-yl]cyclopropane carboxylate (hereinafter "Compound VII").
4-fluoro-3-phenoxybenzyl (±)-trans-2,2-dimethyl-3-[2-methylprop-2-yl)pyrimidin-5-yl]cyclopropane carboxylate (hereinafter "Compound VIII").
(±)-1-cyano-1-(6-phenoxypyrid-2-yl)methyl (±)-trans-2,2-dimethyl-3-(2-prop-2-yl-pyrimidin-5-yl)cyclopropane carboxylate (hereinafter "Compound IX").
(±)-1-cyano-1-(6-phenoxypyrid-2-yl)methyl (±)-trans-2,2-dimethyl-3-(2-cyclohexylpyrimidin-5-yl)cyclopropane carboxylate (hereinafter "Compound X").
(±)-1-cyano-1-(6-phenoxypyrid-2-yl)methyl (+)-trans-2,2-dimethyl-3-(2-cyclopropylpyrimidin-5-yl)cyclopropane carboxylate (hereinafter "Compound XI").
(±)-1-(6-phenoxypyrid-2-yl)ethyl (±)-trans-2,2-dimethyl-3-[2-(2-methylprop-2-yl)pyrimidin-5-yl]cyclopropane carboxylate (hereinafter "Compound XII").
pentafluorobenzyl (±)-trans-2,2-dimethyl-3-[2-(2-methylprop-2-yl)pyrimidin-5-yl]cyclopropane carboxylate (hereinafter "Compound XIII").
(±)-α-ethynyl-3-phenoxybenzyl (±)-trans-2,2-dimethyl-3-[2-(2-methylpropyl-2-yl)pyrimidin-5-yl]-cyclopropane carboxylate (hereinafter "Compound XIV").
4-methoxymethyl-2,3,5,6-tetrafluorobenzyl (±)-trans-2,2-dimethyl-3-[2-(2-methylprop-2-yl)pyrimidin-5-yl]cyclopropane (hereinafter "Compound XV").
2-methyl-3-phenylbenzyl (±)-trans-2,2-dimethyl-3-(2-prop-2-ylpyrimidin-5-yl)cyclopropane carboxylate (hereinafter "Compound XVI").

The insecticidally active compounds of the invention according to Formula I are esters and may be prepared by conventional esterification processes, of which the following are examples.

(a) An acid of formula:

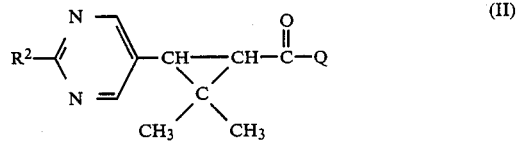

(II)

where Q represents the hydroxy group and R² has any of the meanings given hereinabove, may be reacted directly with an alcohol of formula R¹—OH (III) where R¹ has any of the meanings given hereinabove, the reaction preferably taking place in the presence of an acid catalyst, for example, dry hydrogen chloride, or a dehydrating agent, such as for example, dicyclohexyl carbodiimide.

(b) An acid halide of formula II where Q represents a halogen atom, preferably a chlorine atom, and R² has any of the meanings given hereinabove, may be reacted with an alcohol of formula III, the reaction preferably taking place in the presence of a base, for example, pyridine, alkali metal hydroxide or carbonate, or alkali metal alkoxide.

(c) An acid of formula II where Q represents the hydroxy group or, preferably, an alkali metal salt thereof, may be reacted with halide of formula Q¹—R¹ (IV) wherein Q¹ represents a halogen atom, preferably the chlorine atom, and R¹ has any of the meanings given hereinabove, or with the quaternary ammonium salts derived from such halides with tertiary amines, for example pyridine, or trialkyl amines such as triethylamine.

(d) A lower alkyl ester of formula (II) where Q represents a lower alkoxy group containing up to six carbon atoms, preferably the methoxy or ethoxy group, and R² has any of the meanings given hereinabove, is heated with an alcohol of formula III to effect a transesterification reaction. Preferably the process is performed in the presence of a suitable catalyst, for example, an alkali metal alkoxide, such as sodium methoxide, or an alkylated titanium derivative, such as tetramethyl titanate.

All of these conventional processes for the preparation of esters may be carried out using solvents and diluents for the various reactants where appropriate, and may be accelerated or lead to higher yields of product when performed at elevated temperatures or in the presence of appropriate catalysts, for example phase-transfer catalysts.

The preparation of individual isomers may be carried out in the same manner but commencing from the corresponding individual isomers of compounds of formula II. These may be obtained by conventional isomer separation techniques from mixtures of isomers. Thus cis and trans isomers may be separated by fractional crystallisation of the carboxylic acids or salts thereof, whilst the various optically active species may be obtained by fractional crystallisation of salts of the acids with optically active amines, followed by regeneration of the optically pure acid. The optically pure isomeric form of the acid (or its equivalent acid chloride or ester) may then be reacted with the appropriate alcohol to produce a compound of formula I in the form of an individually pure isomer thereof.

The compounds of formula I may be used to combat and control infestations of insect pests and also other invertebrate pests, for example, acarine pests. The insect and acarine pests which may be combatted and controlled by the use of the invention compounds include those pests associated with agriculture (which term includes the growing of crops for food and fibre products, horticulture and animal husbandry), forestry, the storage of products of vegetable origin, such as fruit, grain and timber, and also those pests associated with the transmission of diseases of man and animals.

In order to apply the compounds of the locus of the pests they are usually formulated into compositions which include in addition to the insecticidally active ingredient or ingredients of formula I suitable inert diluent or carrier materials, and/or surface active agents. The compositions may also comprise another pesticidal material, for example another insecticide or acaricide, or a fungicide, or may also comprise an insecticide synergist, such as for example dodecyl imidazole, safroxan, or piperonyl butoxide.

The compositions may be in the form of dusting powders wherein the active ingredient is mixed with a solid diluent or carrier, for example kaolin, bentonite, kieselguhr, or talc, or they may be in the form of granules, wherein the active ingredient is absorbed in a porous granular material for example pumice.

Alternatively the compositions may be in the form of liquid preparations to be used as dips or sprays, which are generally aqueous dispersions or emulsions of the active ingredient in the presence of one or more known wetting agents, dispersing agents or emulsifying agents (surface active agents).

Wetting agents, dispersing agents and emulsifying agents may be of the cationic, anionic or non-ionic type. Suitable agents of the cationic type include, for example, quaternary ammonium compounds, for example cetyltrimethyl ammonium bromide. Suitable agents of the anionic type include, for example, soaps, salts of aliphatic monoesters of sulphuric acid, for example sodium lauryl sulphate, salts of sulphonated aromatic compounds, for example sodium dodecylbenzenesulphonate, sodium, calcium or ammonium lignosulphonate, or butylnaphthalene sulphonate, and a mixture of the sodium salts of diisopropyl- and triisopropylnaphthalene sulphonates. Suitable agents of the nonionic type include, for example, the condensation products of ethylene oxide with fatty alcohols such as oleyl alcohol or cetyl alcohol, or with alkyl phenols such as octyl phenol, nonyl phenol and octyl cresol. Other non-ionic agents are the partial esters derived from long chain fatty acid and hexitol anhydrides, the condensation products of the said partial esters with ethylene oxide, and the lecithins.

The compositions may be prepared by dissolving the active ingredient in a suitable solvent, for example, a ketonic solvent such as diacetone alcohol, or an aromatic solvent such as trimethylbenzene and adding the mixture so obtained to water which may contain one or more known wetting, dispersing or emulsifying agents.

Other suitable organic solvents are dimethyl formamide, ethylene dichloride, isopropyl alcohol, propylene glycol and other glycols, diacetone alcohol, toluene, kerosene, white oil, methylnaphthalene, xylenes and trichloroethylene, N-methyl-2-pyrrolidone and tetrahydrofurfuryl alcohol (THFA).

The compositions which are to be used in the form of aqueous dispersions or emulsions are generally supplied in the form of a concentrate containing a high proportion of the active ingredient or ingredients, the said concentrate to be diluted with water before use. These concentrates are often required to withstand storage for prolonged periods and after such storage, to be capable of dilution with water to form aqueous preparations which remain homogeneous for a sufficient time to enable them to be applied by conventional spray equipment. The concentrates may contain 10–85% by weight of the active ingredient or ingredients. When diluted to form aqueous preparations such preparations may contain varying amounts of the active ingredient depending upon the purpose for which they are to be used. For agricultural or horticultural purposes, an aqueous preparation containing between 0.0001% and 0.1% by weight of the active ingredient is particularly useful.

In use the compositions are applied to the pests, to the locus of the pests, to the habitat of the pests, or to growing plants liable to infestation by the pests, by any of the known means of applying pesticidal compositions, for example, by dusting or spraying.

The compositions of the invention are toxic to a variety of insect and other invertebrate pests, including, for example, the following:

*Myzus persicae* (aphids)
*Aphis fabae* (aphids)
*Megoura viceae* (aphids)
*Aedes aegypti* (mosquitoes)
*Dysdercus fasciatus* (capsids)
*Musca domestica* (houseflies)
*Pieris brassicae* (white butterfly, larvae)
*Plutella maculipennis* (diamond back moth, larvae)
*Phaedon cochleariae* (mustard beetle)
*Tetranychus cinnabarinus* (carmine spider mite)
*Tetranychus urticae* (red spider mites)
*Aonidiella spp.* (scale insects)
*Trialeuroides spp.* (white flies)
*Blattella germanica* (cockroaches)
*Spodoptera littoralis* (cotton leaf worm)
*Heliothis virescens* (tobacco budworms)
*Chortiocetes terminifera* (locusts)
*Diabrotica spp.* (rootworms)
*Agrotis spp.* (cutworms)
*Chilo partellus* (maize stem borers)

The compounds of formula I and compositions comprising them have shown themselves to be particularly useful in controlling acarine pests of plants such as red mites and rust mites as well as lepidopteran pests of cotton, for example *Spodoptera spp.* and *Heliothis spp.* The compounds may also be used to combat pests which inhabit the soil, for example *Diabrotica spp.* They may also be useful in combating insect and acarine pests which infest domestic animals, such as *Lucilia sericata*, and ixodid ticks such as *Boophilus spp., Ixodes spp., Amblyomma spp., Rhipicephalus spp.,* and *Dermaceutor spp.* They may be effective in combating both susceptible and resistant strains of these pests in their adult, larval and intermediate stages of growth, and may be applied to the infested host animal by topical, oral or parenteral administration.

The following Examples illustrate various aspects of this invention. In the preparation Examples the products were usually identified and characterised by means of nuclear magnetic resonance spectroscopy and infra red spectroscopy. In each case where a product is specifically named its spectral characteristics are consistent with the assigned structure.

EXAMPLE 1

This Example illustrates the preparation of pivalamidine hydrochloride.

A stirred mixture of trimethylacetonitrile (43 g; 0.51M) and dry ethanol (24 g, 0.51M) was cooled using an ice/salt bath whilst dry hydrogen chloride gas was passed into the mixture over a period of 90 minutes, until a total of 21 gms had been taken up. The mixture was then kept for 2 days at the ambient temperature after which it was diluted with dry diethyl ether (500 cm$^3$) to precipitate ethyl trimethyl acetimidate hydrochloride which was collected by filtration (34.5 g). To this was added portionwise a solution of dry ammonia gas (6 g) in dry ethanol (50 cm$^3$) with vigorous stirring. The solid gradually dissolved during the course of the addition and the resultant solution was kept at the ambient temperature for 20 hours after which the solvent was removed by evaporation under reduced pressure and the residual solid washed with diethyl ether to yield pivalamidine hydrochloride (23 g).

EXAMPLE 2

This Example illustrates the preparation of 5-bromo-2-(2-methylprop-2-yl)pyrimidine-4-carboxylic acid.

A solution of sodium ethoxide in ethanol (14.5 cm$^3$ of the solution obtained by dissolving sodium (1.38 g) in dry ethanol (24 cm$^3$)) was added carefully to a stirred mixture of pivalamidine hydrochloride (5.18 g) and dry ethanol (5 cm$^3$) at 40° C. After stirring the mixture for a further 10 minutes a solution of mucobromic acid (5.4 cm$^3$ of the solution obtained by dissolving mucobromic acid (5.16 g) in dry ethanol (8.0 cm$^3$)) was added to the mixture resulting in an exothermic reaction during which the temperature rose to 65° C. After a period the temperature had reduced to 50° C. and the remainder of the sodium ethoxide solution and the remainder of mucobromic acid solution were added. The reaction temperature was maintained at 50° C. for 1 hour by external heating, after which the insoluble portion was removed by filtration at that temperature, washed with ethanol and the washings and filtrate combined. After removing the solvent by evaporation under reduced pressure the residual solid was washed with dilute hydrochloric acid (2M, 10 cm$^3$), with water and dried to yield 5-bromo-2(2-methylpro-2-yl)pyrimidine-4-carboxylic acid (3.8 g), melting point 142°–144° C. (with decomposition) N.m.r and infrared spectra were consistent with this identification.

$^1$H NMR (CDCl$_3$) δ: 1.45 (s, 9H); 9.05 (s, 1H); 9.44 (broad s, 1H).

Infra red (paraffin mull): 2940, 2860, 2500 (broad), 1710, 1570, 1370, 1305, 1290, 1220, 1190, 1175, 750, 680 cm$^{-1}$.

EXAMPLE 3

This Example illustrates the preparation of 5-bromo-2-(2-methylprop-2-yl)pyrimidine.

5-Bromo-2-(2-methylprop-2-yl)pyrimidine-4-carboxylic acid (1.0 g) was heated with stirring at 145° C. after which the decarboxylated product was obtained by distillation using a Kugelrohr apparatus under water pump pressure. The distillate solidified on cooling to yield 5-bromo-2-(2-methylprop-2-yl)pyrimidine (0.6 g) melting point 50°–51° C. N.m.r. and infra-red spectra were consistent with this identification.

$^1$H nmr (CDCl$_3$) δ: 1.39 (s, 9H); 8.71 (s, 2H).

Infra red (paraffin mull): 2940, 2860, 1530, 1480, 1420, 1170, 1010, 810, 640 cm$-1$.

EXAMPLE 4

This Example illustrates the preparation of 2-(2-methylprop-2-yl)pyrimidine-5-carboxaldehyde.

A solution of 5-bromo-2-(2-methylprop-2-yl)pyrimidine (7.6 g, 0.035M) in dry tetrahydrofuran (50 cm$^3$) was added in small portions to magnesium turnings (0.95 g, Grignard grade) in the presence of a few crystals of iodine. The rate of addition was controlled by the rate of the exothermic reaction. When the addition was complete the mixture was warmed to complete the reaction. After cooling the mixture of 5° C., a solution of dimethyl formamide (2.58 g) in tetrahydrofuran (15 ml) was added thereto dropwise. The mixture was allowed to warm to the ambient temperature with stirring over a period of 2 hours and kept for 16 hours without stirring. After adding water (5 cm$^3$) to the mixture the tetrahydrofuran was removed by evaporation under reduced pressure and the residue partitioned between dilute aqueous ammonium chloride solution (100 cm$^3$) and diethyl ether (150 cm$^3$). The aqueous phase was extracted with ether (150 cm$^3$) and the extract combined with the ether phase, washed with water, and dried over anhydrous magnesium sulphate. Evaporation of the ether under reduced pressure yielded an oily solid residue (5.8 g) which was purified by dry column chromatography using a silica column eluted with a mixture of methylene chloride (100 parts by volume) and ethyl acetate (2 parts by volume) to give 2-(2-methylprop-2-yl)pyrimidine-5-carboxaldehyde (3.4 g) melting point 82°–83° C.

Infra red (paraffin mull): 2940, 2860, 1700, 1590, 1430, 1230, 1150, 860, 650 cm$^{-1}$.

EXAMPLE 5

This Example illustrates the preparation of ethyl 3-[2-(1,1-dimethylethyl)pyrimidin-5-yl]propenoate.

A solution of 0,0-diethyl ethoxycarbonylmethylphosphonate (3.93 g) in dry diethyl ether (20 cm$^3$) was added dropwise to a stirred suspension of sodium hydride (0.54 g of a 50% oil dispersion) in dry diethyl ether (30 cm$^3$) at −5° C. and the mixture stirred thereafter for a further period of 90 minutes. A solution of 2-(2-methylprop-2-yl)pyrimidine-5carboxaldehyde (2.88 g) in dry diethyl ether (40 cm$^3$) was added dropwise to this stirred mixture at 0° C., the resultant mixture allowed to warm to the ambient temperature with stirring over 2 hours after which it was kept at the ambient temperatures for 16 hours. The mixture was partitioned between water (150 cm³) and diethyl ether (250 cm³), the aqueous phase extracted with ether (250 cm³) and the extracts combined with the ethereal phase. After washing with water (200 cm³) and drying over anhydrous magnesium sulphate, the solvent was evaporated under reduced pressure and residual oil subjected to dry column chromatography using a silica column and, as eluent, dichloromethane containing 5% v/v ethyl acetate, to yield ethyl 3-[2-(2-methylprop-2-yl)pyrimidin-5-yl]propenoate (3.6 g) which solidified on standing, melting point 43°–45° C. N.m.r. and infra-red spectral data indicate the product as consisting of the trans isomer.

$^1$H NMR (CDCl$_3$) δ: 1.35 (t, 3H); 1.42 (s, 9H); 4.24 (q, 2H); 6.50 (d, 1H); 7.60 (d, 1H); 8.82 (s, 2H).

Infra red (paraffin mull): 2960, 1730, 1645, 1590, 1485, 1440, 1320, 1185, 1155 cm$^{-1}$.

EXAMPLE 6

This Example illustrate the preparation of ethyl trans-2,2-dimethyl-3-[2-(2-methylprop-2-yl)pyrimidin-5-yl]cyclopropane carboxylate.

A solution of n-butyllithium (10.6 cm³ of a 1.55M solution in hexane) was added slowly to a stirred solution of prop-2-yl triphenyl phosphonium iodide (7.1 g) in dry tetrahydrofuran (20 cm³) at the ambient temperature under a nitrogen atmosphere and the resultant mixture stirred for a further 15 minutes after which a solution of ethyl trans 3-[2-(2-methylprop-2-yl)pyrimidin-5-yl]propenoate (3.2 g) in dry tetrahydrofuran (25 cm³) was added dropwise at −5° C. After stirring for a further period of 30 minutes during which time the mixture warmed to the ambient temperature it was kept at the ambient temperature for 16 hours. The mixture was partitioned between water (300 cm³) and diethyl ether (200 cm³) and the aqueous phase extracted with ether (2×200 cm³) and the extracts combined with the ethereal phase. After washing with water (2×100 cm³) and drying over anhydrous magnesium sulphate, the ether was removed by evaporation under reduced pressure to yield a residual oil which was subjected to dry column chromatography using a silica column eluted first with dichloromethane (to remove triphenyl phosphine) and then with a mixture of dichloromethane (100 parts by volume) and ethyl acetate (5 parts by volume) to yield ethyl trans-2,2-dimethyl-3-[2-(2-methylprop-2-yl)pyrimidin-5-yl]cyclopropane carboxylate (2.8 g), the identity of which was confirmed by infra red and n.m.r. spectroscopy.

$^1$H NMR (CDCl$_3$) δ: 0.99 (s, 3H); 1.31 (t, 3H); 1.40 (s, 12H); 1.96 (d, 1H); 2.54 (d, 1H); 4.2 (q, 2H); 8.5 (s, 2H).

Infra red (liquid film): 2960, 1730, 1485, 1450, 1420, 1260, 1180, 1165 cm$^{-1}$.

Mass spectroscopy (M+): 276.

EXAMPLE 7

This Example illustrates the preparation of trans-2,2-dimethyl-3-[2-(2-methylprop-2-yl)pyrimidin-5-yl]cyclopropane carboxylic acid.

A solution of ethyl trans-2,2-dimethyl-3-[2-(2-methylprop-2-yl)pyrimidin-5-yl]cyclopropane carboxylate (2.6 g) in ethanol (50 cm³) was mixed with a solution of sodium hydroxide (1.0 g) in water (50 cm³) and the mixture stirred at the ambient temperature for 5 hours. After removal of the bulk of the ethanol by evaporation under reduced pressure the pH of the residual mixture was adjusted to 3 with dilute hydrochloric acid. The mixture was extracted with diethyl ether (2×200 cm³), and the combined extracts washed with water and dried over anhydrous magnesium sulphate. Evaporation of the ether under reduced pressure yielded trans-2,2-dimethyl-3-[2-(2-methylprop-2-yl)pyrimidin-5-yl]cyclopropane carboxylic acid (2.1 g), melting point 168°–9° C.

$^1$H NMR (CDCl$_3$) δ: 1.03 (s, 3H); 1.41 (s, 9H); 1.48 (s, 3H); 2.02 (d, 1H); 2.6 (d, 1H); 8.57 (s, 2H).

Infra red (paraffin mull): 2940, 1700, 1485, 1430, 1335, 1250, 1230, 1210 cm$^{-1}$.

Mass spectroscopy (M+): 248.

EXAMPLE 8

This Example illustrates the preparation of 3-phenoxybenzyl trans-2,2-dimethyl-3-[2-(2-methylprop-2-yl)pyrimidin-5-yl]cyclopropane carboxylate.

A mixture of trans-2,2-dimethyl-3-[2-(2-methylprop-2-yl) pyrimidin-5-yl]cyclopropane carboxylic acid (500 mg), 3-phenoxybenzylbromide (552 mg), anhydrous potassium carbonate (304 mg) and acetone (10 cm³) was heated at the reflux temperature for 2 hours with stirring after which it was kept at the ambient temperature for 16 hours. After removing the solid precipitate by filtration the filtrate was concentrated by evaporation under reduced pressure. The residual oil was subjected to high performance liquid chromatography (Gilson) using a silica column and, as eluent, a mixture of dichloromethane (100 parts by volume) and ethyl acetate (2 parts by volume). The product, 3-phenoxybenzyl trans-2,2-dimethyl-3-[2-(2-methylprop-2-yl)-pyrimidin-5-yl]cyclopropane carboxylate (800 mg) was obtained as an oil and identification was confirmed by n.m.r. and infra red spectroscopy.

$^1$H NMR (CDCl$_3$) δ: 0.98 (s, 3H); 1.40 (s, 12H); 2.02 (d, 1H); 2.56 (d, 1H); 5.15 (s, 2H); 6.8–7.5 (m, 9H).

Infra red (liquid film): 2960, 1730, 1590, 1490, 1260, 1220, 1160 cm$^{-1}$.

Mass spectroscopy (M+): 430.

EXAMPLE 9

This Example illustrates the preparation of 4-allyl-2,3,5,6-tetrafluorobenzyl trans-2,2-dimethyl-3-[2-(2-methylprop-2-yl)pyrimidin-5-yl]cyclopropane carboxylate.

Dicyclohexylcarbodiimide (420 mg) was added in portions to a stirred mixture of trans-2,2-dimethyl-3-[2-(dimethylprop-2-yl)pyrimidin-5-yl]cyclopropane carboxylate (504 mg), 4-allyl-2,3,5,6-tetrafluorobenzyl alcohol (462 mg-containing a minor amount of isomeric 2-allyl-3,4,5,6-tetrafluorobenzyl alcohol), 4-dimethylamino pyridine (5 mg) and dry dichloromethane (10 cm³) at the ambient temperature and the resultant mixture stirred for a further period of 105 minutes after which it was kept at the ambient temperature for 16 hours. The solid precipitate was removed by filtration, washed with ether and the washings combined with the filtrate. After removal of the solvent by evaporation under reduced pressure the residual oil was subjected to HPLC (Gilson) using a silica column and, as eluent, a mixture of dichloromethane (100 parts by volume) and ethyl acetate (2 parts by volume) to give a product consisting of 94% by weight of the 4-allyl-2,3,5,6-tetrafluorobenzyl ester and 6% by weight of the 2-allyl-3,4,5,6-tetrafluorobenzyl ester of trans-2,2-dimethyl-3-[2-(2-methylprop-2-yl)pyrimidin-5-yl]cyclopropane carboxylic acid (650 mg), as an oil which solidified on standing, melting point 64°–66° C. The identification was confirmed by n.m.r., infra red and mass spectroscopic analysis.

$^1$H NMR (CDCl$_3$) δ: 0.99 (s, 3H); 1.39 (s, 12H); 1.96 (d, 1H); 2.56 (d, 1H); 3.5 (m, 2H); 4.9–5.3 (m, 4H); 5.6–6.1 (m, 1H); 8.48 (s, 2H).

Infra red (paraffin mull): 2960, 2930, 2860, 1735, 1490, 1460, 1440, 1420, 1330, 1150 cm$^{-1}$.

Mass spectroscopy (M+): 450.

EXAMPLE 10

By the use of a procedure similar to that described in Example 8 4-methyl-2,3,5,6-tetrafluorobenzyl trans-2,2-dimethyl-3-[2-(2-methylprop-2-yl)pyrimidin-5-yl]cyclopropane carboxylate was obtained as a colourless oil from the carboxylic acid and the benzyl bromide.

$^1$H NMR (CDCl$_3$) δ: 0.99 (s, 3H); 1.39 (s, 12H); 196 (d, 1H); 2.30 (m, 3H); 2.56 (d, 1H); 5.28 (s, 2H); 8.48 (s, 2H).

Infra red (liquid film): 2960, 1740, 1495, 1420, 1290, 1155, 1075 cm$^{-1}$.

Mass spectroscopy (M+): 424.

EXAMPLE 11

By the use of a procedure similar to that described in Example 9 the following esters were obtained:

(a) 6-phenoxypyrid-2-ylmethyl trans-2,2-dimethyl-3-[2-(2-methylprop-2-yl)pyrimidin-5-yl]cyclopropane carboxylate from the carboxylic acid and 6-phenoxypyrid-2-ylmethanol.

$^1$H NMR (CDCl$_3$) δ: 1.01 (s, 3H); 1.41 (s, 12H); 2.08 (d, 1H); 2.58 (d, 1H); 5.18 (s, 2H); 6.7–7.8 (m, 8H); 8.50 (s, 2H).

Infra red (liquid film): 2960, 1730, 1600, 1580, 1490, 1540, 1250, 1160 cm$^{-1}$.

Mass spectroscopy (M+): 431.

(b) 2-methyl-3-phenylbenzyl trans-2,2-dimethyl-3-[2-(2-methylprop-2-yl)pyrimidin-5-yl]cyclopropane carboxylate from the carboxylic acid and 2-methyl-3-phenylbenzyl alcohol.

$^1$H NMR (CDCl$_3$) δ: 0.99 (s, 3H); 1.40 (s, 12H); 2.06 (d, 1H); 2.25 (s, 3H); 2.60 (d, 1H); 5.27 (s, 2H); 7.1–7.5 (m, 8H); 8.50 (s, 2H).

Infra red (liquid film): 2960, 1730, 1485, 1420, 1160, 760, 705 cm$^{-1}$.

Mass spectroscopy (M+): 428.

(c) α-cyano-3-phenoxybenzyl trans-2,2-dimethyl-3-[2-(2-methyl-prop-2-yl)pyrimidin-5-yl]cyclopropane carboxylate from the carboxylic acid and α-cyano-3-phenoxybenzyl alcohol.

$^1$H NMR (CDCl$_3$) δ: 0.99 (s); 1.04 (s); 1.35 (s); 1.39 (s); 1.45 (s); 2.05 (m); 2.6 (m); 6.42 (s); 6.44 (s); 7.26 (m); 8.46 (s); 8.50 (s).

(Integration consistent with 2:1 mixture of diastereoisomers).

Infra red (liquid fim): 2960, 1740, 1590, 1485, 1250, 1140, 695 cm$^{-1}$.

Mass spectroscopy (M+): 455.

(d) 1-cyano-1-(6-phenoxypyrid-2-yl)methyl trans-2,2-dimethyl-3-[2-(2-methylprop-2-yl)pyrimidin-5-yl]cyclopropane carboxylate from the carboxylic acid and 1-cyano-1-(6-phenoxypyrid-2-yl)methanol.

$^1$H NMR (CDCl$_3$) δ: 1.00 (s); 1.02 (s); 1.35 (s); 1.40 (s); 2.1 (m); 2.6 (m); 6.4 (3s); 6.9 (d); 7.2 (m); 7.8 (dd); 8.50 (2s).

(Integration consistent with 1:1 mixture of diastereoisomers).

Infra red (liquid film): 2960, 1745, 1595, 1490, 1450, 1260, 1140, 695 cm$^{-1}$.

Mass spectroscopy (M+): 456

(e) 4-methoxymethyl-2,3,5,6-tetrafluorobenzyl (±)-trans-2,2-dimethyl-3-[2-(2-methylprop-2-yl)pyrimidin-5-yl]-2,2-dimethylcyclopropane carboxylate from the carboxylic acid and 4-methoxymethyl-2,3,5,6-tetra fluorobenzyl alcohol.

$^1$H NMR (CDCl$_3$) δ: 0.99 (s, 3H); 1.40 (2s, 12H); 1.95 (d, 1H); 2.55 (d, 1H); 3.40 (s, 3H); 4.50 (m, 2H); 5.30 (m, 2H); 8.50 (s, 2H).

Infra red (paraffin mull): 1735, 1595, 1490, 1295, 1150, 910, 880, 770 cm$^{-1}$.

Mass spectroscopy (M+): 454.

(f) (±)-1-(6-phenoxypyrid-2-yl)ethyl (±)-trans-2,2-dimethyl-3-[2-(2-methylprop-2-yl)pyrimidin-5-yl]cyclopropane carboxylate from the carboxylic acid and (±)-1-(6-phenoxypyrid-2-yl)ethanol.

$^1$H NMR (CDCl$_3$) δ: 1.0 (s); 1.33 (s); 1.40 (s); 1.5 (s); 1.8 (s); 2.05 (2d); 2.50 (2d); 5.85 (q); 6.7 (d); 7.2 (m); 7.65 (dd); 8.50 (2s).

(Integration consistent with 3:2 mixture of diastereoisomers).

Infra red (liquid film): 2980, 1730, 1600, 1580, 1445, 1260, 1170, 990, 700 cm$^{-1}$.

Mass spectroscopy (MH+): 446

(g) 4-fluoro-3-phenoxybenzyl (±)-trans-2,2-dimethyl-3-[2-(2-methylprop-2-yl)pyrimidin-5-yl]cyclopropane carboxylate from the carboxylate acid and 4-fluoro-3-phenoxybenzyl alcohol.

(h) pentafluorobenzyl (±)-trans-2,2-dimethyl-3-[2-(2-methylprop-2-yl)pyrimidin-5-yl]cyclopropane carboxylate from the carboxylate acid and pentafluorobenzyl alcohol.

(g) (±)-α-ethynyl-3-phenoxybenzyl (±)-trans-2,2-dimethyl-3-[2-(2-methylprop-2-yl)pyrimidin-5-yl]cyclopropane carboxylate from the carboxylic acid and (±)-α-ethynyl-3-phenoxybenzyl alcohol.

EXAMPLE 12

This Example illustrates the preparation of (±)-α-cyano-3-phenoxybenzyl (±)-trans-3-[2-(2-methylprop-2-yl)pyrimidin-5-yl]-2,2-dimethylcyclopropane carboxylate (Compound IV) and separation of its constituent pairs of enantiomeric isomers.

A stirred mixture of (±)-trans-3-[2-(2-methylprop-2-yl)pyrimidin-5-yl]-2,2-dimethylcyclopropane carboxylic acid (3.2 g), 3-phenoxybenzaldehyde cyanhydrin (3.8 g, contaminated with ca. 20% 3-phenoxybenzaldehyde), 4-dimethylaminopyridine (100 mg) and dichloromethane (100 cm$^3$) was treated with portions of dicyclohexyl carbodiimide (2.8 g) at the ambient temperature (ca. 24° C.). After stirring for two hours the mixture was kept at the ambient temperature for 16 hours, filtered and the collected solids washed with dichloromethane. The combined filtrate and washings were concentrated by evaporation of the solvent under reduced pressure and the residual oil purified by h.p.l.c. (Gilson) using a silica column eluted with a mixture of dichloromethane (100 parts by volume) and ethyl acetate (5 parts by volume). The initial fractions yielded a mixture of the desired product with 3-phenoxybenzaldehyde, the later fractions gave pure (±)-α-cyano-3-phenoxybenzyl (±)-trans-3-[2-(2-methylprop-2-yl)pyrimidin-5-yl]-2,2-dimethylcyclopropane carboxylate (5.3 g) in the form of a gum consisting of a mixture of two racemic pairs of enantiomeric isomers in a ratio of 2:1. The initial fractions were rechromatographed using a 2.5 cm silica column and the same eluent at a rate of 30 cm$^3$/minute to give the faster running (less polar) pair of enantiomeric isomers (120 mg). The more polar (faster running) pair of enantiomeric isomers (21 mg) were obtained by similar rechromatography of the later fractions (containing the 2:1 mixture (A) of isomer pairs). The product consisted of a 95:5 mixture of the more polar and less polar isomers. Recombination of rejected fractions and evaporation gave a 7:1 mixture (B) of the less polar and more polar isomers.

In biological tests using adult red spider mites (*Tetranychus urticae*) on french bean leaves the more polar pair of enantiomeric isomers was about ten times more effective ($LC_{50}=4.5$ ppm) than the less polar pair ($LC_{50}=49$ ppm).

A mixture of the less polar and more polar pairs of enantiomeric isomers in a ratio of 7:1 (10 mg) was dissolved in isopropanol (0.1 cm$^3$) containing triethylamine (5% by weight) was stirred at room temperature. After 22.5 hours the ratio was approximately 1:1 due to base induced epimerisation at the α-carbon of the alcohol moiety.

$^1$H NMR (CDCl$_3$) δ: (A) 0.95 (s); 1.0 (s); 1.35 (s); 1.4 (s); 1.45 (s); 2.0 (2d); 2.6 (2d); 6.4 (2s); 7.2 (m); 8.45 (2s).

(Integration consistent with 2:1 mixture of diastereoisomers).

(B) 1.0 (s, 3H); 1.40 (s, 9H); 1.45 (s, 3H); 2.05 (d, 1H); 2.55 (d, 1H); 6.40 (s, 1H); 7.2 (m, 9H); 8.40 (s, 2H).

Infra red (liquid film)

(A) 2960, 1740, 1590, 1490, 1445, 1250, 1140, 695 cm$^{-1}$.

(B) 2960, 1740, 1585, 1480, 1445, 1245, 1140, 695 cm$^{-1}$.

EXAMPLE 13

Preparation of methyl (±)-trans-2,2-dimethyl-3-formyl cyclopropane carboxylate.

A mixture of methyl 2,2-dimethyl-3-(dimethoxymethyl)cyclopropane carboxylate (95% (±)-trans-isomer: 40.0 g), glacial acetic acid (120 cm$^3$), acetone (160 cm$^3$) and water (280 cm$^3$) was stirred at the ambient temperature for 5 hours, diluted with water (1500 cm$^3$) and extracted with diethyl ether (1000 cm$^3$). The aqueous residue was washed with ether (2×500 cm$^3$) and the washings and extracts washed with saturated sodium bicarbonate solution until free of acidity. After drying the ethereal solution over anhydrous magnesium sulphate the solvent was removed by evaporation to yield a residual oil which was purified by distillation and methyl (±)-trans-2,2-dimethyl-3-formylcyclopropane carboxylate (28.5 g) collected as the fraction boiling at 46°–48° C./0.05 mm Hg.

EXAMPLE 14

Preparation of (±)-trans methyl 3-[(E,Z)-2-methoxyvinyl]-2,2-dimethylcyclopropane carboxylate.

Sodium hydride (obtained by washing a 50% oil dispersion (9.6 g) with n-hexane to remove the oil) was suspended in dry dimethylsulphoxide (150 cm$^3$, freshly distilled from calcium hydride) and the suspension stirred under a dry nitrogen atmosphere at 38°–40° C. for 5 hours. A solution of methoxymethyl triphenyl phosphonium chloride (68.8 g) in dry dimethylsulphoxide (200 cm$^3$) was added over 15 minutes whilst the reaction temperature was maintained at ca. 20° C. by external cooling. The solution of the ylid thus produced was added dropwise to a stirred solution of methyl (±)-trans-2,2-dimethyl-3-formylcyclopropane carboxylate (28.5 g, freshly distilled) in dimethylsulphoxide (50 cm$^3$) whilst keeping the reaction temperature at ca. 20° C. over a period of 2 hours. The mixture was stirred for a further 30 minutes and then kept at the ambient temperature for 72 hours. Water (1500 cm$^3$) was added, and the mixture extracted with diethyl ether (1×1000 cm$^3$), 2×500 cm$^3$). The extracts were combined, washed with water (3×300 cm$^3$) and dried over anhydrous magnesium sulphate. The solvent was removed by evaporation under reduced pressure and the residue triturated with petroleum ether (boiling range 60°–80° C., 150 cm$^3$). The undissolved solid was removed by filtration and the filtrate evaporated to give a yellow oil (29.0 g) which was distilled under reduced pressure using a Kugelrohr apparatus to yield methyl (±)-trans-3-[(E,Z)-2-methoxyvinyl]-2,2-dimethylcyclopropane carboxylate (21.4 g), boiling point 64° C./0.05 mm Hg.

$^1$H NMR (CDCl$_3$) δ: 1.13 (s); 1.24 (s); 1.26 (s); 1.4 (m); 1.9 (m); 2.3 (m); 3.5 (s); 3.6 (s); 3.66 (s); 4.1 (2d); 4.56 (2d); 6.0 (dd); 6.4 (d).

(Integration consistent with 2:1 mixture of (E) and (Z) isomers).

Infra red (liquid film): 2960, 1730, 1650, 1440, 1270, 1235, 1170, 920 cm$^{-1}$.

EXAMPLE 15

This example illustrates the preparation of a mixture of methyl (±)-trans-3-[(E,Z)-2-dimethylamino-1-formylvinyl]-2,2-dimethylcyclopropane carboxylate and methyl (±)-trans-3-[(E,Z)-formyl-2-methoxyvinyl]-2,2-dimethylcyclopropane carboxylate.

A solution of phosphoryl chloride (12.0 cm$^3$) in 1,2-dichloroethane (10.0 cm$^3$) was added dropwise to a stirred mixture of dimethylformamide (29.5 cm$^3$) and 1,2-dichloroethane (100 cm$^3$) at the ambient temperature. When the addition was complete the mixture was stirred for a further 15 minutes and cooled to 15° C. To this mixture was added portionwise a solution of methyl (±)-trans-3-[(E,Z)-2-methoxyvinyl]-2,2-dimethylcyclopropane carboxylate (10.0 g) in 1,2-dichloroethane (80 cm$^3$). The mixture was kept at the ambient temperature for 16 hours and solid anhydrous potassium carbonate (150 g) and ice added. When the exothermic reaction had subsided the mixture was extracted with methylene chloride (2×300 cm$^3$) and extracts combined and washed with water (300 cm$^3$). After drying over anhydrous magnesium sulphate the solvent was removed by evaporation under reduced pressure and the residual oil heated at 55° C. and 0.05 mm Hg in a Kugelrohr apparatus to remove the volatile components to yield a mixture containing a minor amount of methyl (±)-trans-3-[(E,Z)-1-formyl-2-methoxyvinyl]-2,2-dimethylcyclopropane carboxylate and a major amount of methyl (±)-trans-3-[(E,Z)-1-dimethylamino-1-formylvinyl]-2,2-dimethylcyclopropane carboxylate (A), (10.3 g).

$^1$H NMR (CDCl$_3$) δ: (A) 1.0 (s); 1.05 (s); 1.27 (s); 1.30 (s); 2.0 (m); 3.18 (s); 3.37 (s); 3.68 (s); 3.70 (s); 6.75 (broad s); 8.35 (broad s); 8.8 (s).

(Integration consistent with 2:1 mixture of (E) and (Z) insomers).

Infra red (paraffin mull): 2960, 2720, 1730, 1600, 1450, 1410, 1280, 1230, 1175 cm$^{-1}$.

EXAMPLE 16

This Example illustrates the preparation of methyl-(±)-trans-3-(2-cyclohexylpyrimidin-5-yl)cyclopropane carboxylate.

Sodium methoxide (3.2 cm$^3$ of a 2M solution in methanol) was added dropwise to a stirred mixture of methyl (±)-trans-3-[(E,Z)-2-dimethylamino-1-formylvinyl]-

2,2-dimethylcyclopropane carboxylate (1.0 g; in the form of the product of Example 15 containing a minor proportion of methyl (±)-trans-3-[E,Z-1-formyl-2-methoxyvinyl]-2,2-dimethylcyclopropane carboxylate), cyclohexanoyl amidine (1.08 g) and methanol (8 cm³) at the ambient temperature and the resultant mixture heated at the reflux temperature for 3.5 hours. The mixture was cooled to the ambient temperature and poured into water (200 cm³) and extracted with diethyl ether (2×200 cm³). After washing the combined extracts with water (50 cm³) and drying over anhydrous magnesium sulphate, the solvent was removed by evaporation under reduced pressure the residual oil was purified by column chromatography using silica column eluted with a mixture of methylene chloride (3 parts by volume) an diethyl ether (1 part by volume) to yield methyl (±)-trans-3-[(E,Z)-2-dimethylamino-1-formylvinyl]-2,2-dimethylcyclopropane carboxylate (790 mg).

$^1$H NMR (CDCl$_3$) δ: 1.0 (s, 3H); 1.4 (s, 3H); 1.2–1.8 (b, 10H); 1.95 (d, 1H); 2.5 (d, 1H); 2.8 (b, 1H); 3.7 (s, 3H); 8.5 (s, 2H).

Infra red (liquid fim): 2940, 2860, 1730, 1600, 1500, 1440, 1290, 1175 cm$^{-1}$.

EXAMPLE 17

The product of Example 16 (790 mg) was converted to (±)-trans-3-(2-cyclohexylpyrimidin-5-yl)-2,2-dimethylcyclopropane carboxylic acid (750 mg, m.p. 128°–130° C.) by the use of a procedure similar to that described in Example 7 except that methanol was used in place of ethanol.

Infra red (paraffin mull): 3500–2200 (broad), 1710, 1550, 1340, 1290, 1260, 1190, 1120 cm$^{-1}$.

Mass spectroscopy (M+): 274.

EXAMPLE 18

This Example illustrates the preparation of (RS)-1-cyano-1-(6-phenoxypyrid-2-yl)methyl (1RS, trans)-3-(2-cyclohexylpyrimidin-5-yl)-2,2-dimethylcyclopropane carboxylate.

Dicyclohexylcarbodimide (118 mg) was added to a stirred mixture of (±)-trans-3-(2-cyclohexylpyrimidine-5-yl)-2,2-dimethylcyclopropane carboxylate (150 mg), 1-cyano-1-(6-phenoxypyrid-2-yl)methanol (130 mg), 4-dimethylaminopyridine (5 mg) and dichloromethane (5 cm³) and the mixture stirred at the ambient temperature for 7 hours, and kept for a further 16 hours without stirring. The product was isolated by filtering through a silica column, eluting first with dichloromethane and then with a mixture of dichloromethane (20 parts by volume) and ethyl acetate (1 part by volume) to yield. (RS)-1-cyano-1-(6-phenoxypyrid-2-yl)methyl (1RS, trans)-3-(2-cyclohexylpyrimidine-5-yl)-2,2-dimethylcyclopropane carboxylate, (248 mg) identified by n.m.r. as a 1:1 mixture of the two pairs of enantiomeric diastereomers.

$^1$H NMR (CDCl$_3$) α: 1.0 (2s); 1.35 (s); 1.43 (s); 1.2–2.0 (bm); 2.05 (m); 2.6 (m); 2.85 (m); 6.35 (bs); 6.9 (d); 7.25 (m); 7.8 (dd); 8.45 (2s).

(Integration consistent with 1:1 mixture of diastereomers).

Infra red (liquid film): 2940, 2860, 1745, 1600, 1450, 1150, 810, 700 cm$^{-1}$.

EXAMPLE 19

By the use of procedures similar to that described in Example 16, the following compounds were also prepared from the relevant amidines.

(i) Methyl (±)-trans-3-(2-prop-2-ylpyrimidin-5-yl)-2,2-dimethylcyclopropane carboxylate.

$^1$H NMR (CDCl$_3$) δ: 0.98 (s, 3H); 1.30 (s, 3H); 1.38 (s, 3H); 1.40 (s, 3H); 1.95 (d, 1H); 2.25 (d, 1H); 3.2 (m, 1H); 3.75 (s, 1H); 8.48 (s, 2H).

Infra red (liquid film): 2980, 1735, 1595, 1550, 1440, 1340, 1260, 1175, 830 cm$^{-1}$.

(ii) Methyl (±)-trans-3-(2-cyclopyropylpyrimidin-5-yl)-2,2-dimethylcyclopropane carboxylate.

$^1$H NMR (CDCl$_3$) δ: 0.96 (s, 3H); 1.05 (m, 4H); 1.40 (s, 3H); 1.95 (d, 1H); 2.2 (m, 1H); 2.5 (d, 2H); 3.75 (s, 3H); 8.4 (s, 2H).

Infra red (liquid film): 3010, 2960, 1730, 1600, 1550, 1470, 1445, 1175, 915 cm$^{-1}$.

EXAMPLE 20

By the use of procedures similar to that described in Examples 17 and 18 the following insecticidal and acaricidal compound of formula I were obtained.

(i) 2-methyl-3-phenylbenzyl (±)-trans-2,2-dimethyl-3-(2-prop-2-ylpyrimidin-5-yl)cyclopropane carboxylate.

$^1$H NMR (CDCl$_3$) δ: 0.99 (s, 3H); 1.30 (s, 3H); 1.38 (s, 3H); 1.42 (s, 3H); 2.1 (d, 1H); 2.25 (s, 3H); 2.65 (d, 1H); 3.2 (m, 1H); 5.27 (s, 2H); 7.3 (m, 8H); 8.49 (s, 2H).

Infra red (liquid film): 2980, 1730, 1595, 1550, 1425, 1240, 1165, 740, 710 cm$^{-1}$.

(ii) (±)-1-cyano-1-(6-phenoxypyrid-2-yl)methyl (±)-trans-2,2-dimethyl-3-(2-prop-2-ylpyrimidin-5-yl)cyclopropane carboxylate.

$^1$H NMR (CDCl$_3$) δ: 1.00 (s); 1.03 (s); 1.31 (s); 1.36 (s); 1.38 (s); 1.42 (s); 2.05 (m); 2.60 (m); 3.2 (m); 6.35 (bs); 6.9 (d); 7.3 (m); 7.8 (dd); 8.5 (2s).

(Integration consistent with 1:1 mixture of diastereisomers).

Infra red (liquid film): 2980, 1745, 1595, 1580, 1450, 1280, 1150, 745, 700 cm$^{-1}$.

(iii) (±)-1-cyano-1-(6-phenoxypyrid-2-yl)methyl (±)-trans-2,2-dimethyl-3-(2-cyclopropylpyrimidin-5-yl)cyclopropane carboxylate.

$^1$H NMR (CDCl$_3$) δ: 1.0 (s); 1.03 (m); 1.06 (s); 1.34 (s); 1.42 (s); 2.0 (2d); 2.2 (m); 28 (m); 6.4 (s); 6.9 (d); 7.3 (m); 7.8 (dd); 8.35 (2s).

(Integration consistent with 1:1 mixture of diastereoisomers).

Infra red (liquid film): 3010, 2940, 1750, 1600, 1450, 1260, 1150, 910, 800, 700 cm$^{-1}$.

EXAMPLE 21

The insecticidal activity of Compounds I to VII is set out in the following Table as a grading of A, B or C where A indicates that 80–100% mortality was observed, B indicates that 50–79% mortality was observed and C indicates that 0–49% mortality was observed. The tests were conducted by supporting the test species on a medium (eg. leaves of a suitable food plant, or filter paper) and spraying the pests and medium (contact test-"CT" in the Table) or by spraying the medium before placing the pests thereon (residual test-"RT" in the Table). Assessment of mortality was made 72 hours after spraying except for houseflies (*Musca domestica*) where the assessment was made after 24 hours. In the test the compounds were used in the form of aqueous composition comprising 500 parts per million of the compound prepared by dissolving the compound in mixture of solvents consisting of 4 parts by volume by acetone and 1 part by volume of diacetone alcohol and diluting the solution with water containing 0.01% by weight of a wetting agent ("Lissapol" NX-"Lissapol" is a Registered Trade Mark).

TABLE I

| TEST SPECIES | STAGE | SUPPORT MEDIUM | TYPE OF TEST | COMPOUND | | | | | | | |
|---|---|---|---|---|---|---|---|---|---|---|---|
| | | | | I | II | III | IV | V | VI | VII | VIII |
| *Tetranychus urticae* (red spider mites) | adults | French bean leaves | CT | A | A | A | A | A | A | A | A |
| *Tetranychus urticae* (red spider mites) | eggs | French bean leaves | CT | A | A | C | A | A | A | A | A |
| *Myzus persicae* (peach aphids) | mixed | Broad bean leaves | CT | A | A | A | B | A | A | A | A |
| *Chilo partellus* (maize stem borers) | larvae | Oil seed rape leaves | RT | A | A | A | A | A | A | A | A |
| *Heliothis virescens* (tobacco budworms) | larvae | Cotton leaves | RT | A | C | C | A | A | A | A | A |
| *Diabrotica balteata* (rootworms) | larvae | Filter paper/ maize seed | RT | C | A | A | A | A | A | C | A |
| *Musca domestica* (houseflies) | adults | Cotton wool/ sucrose | CT | C | A | A | B | C | B | C | C |
| *Blatella germanica* (cockroaches) | adults | Filter paper | RT | A | C | C | A | C | A | C | C |

| TEST SPECIES | STAGE | SUPPORT MEDIUM | TYPE OF TEST | COMPOUND | | | | | | | |
|---|---|---|---|---|---|---|---|---|---|---|---|
| | | | | IX | X | XI | XII | XIII | XIV | XV | XVI |
| *Tetranychus urticae* (red spider mites) | adults | French bean leaves | CT | B | A | C | A | A | A | A | A |
| *Tetranychus urticae* (red spider mites) | eggs | French bean leaves | CT | A | C | A | A | C | A | C | C |
| *Myzus persicae* (peach aphids) | mixed | Broad bean leaves | CT | C | C | C | A | A | A | A | B |
| *Chilo partellus* (maize stem borers) | larvae | Oil seed rape leaves | RT | A | C | A | A | A | A | A | A |
| *Heliothis virescens* (tobacco budworms) | larvae | Cotton leaves | RT | C | C | C | A | A | A | C | A |
| *Diabrotica balteata* (rootworms) | larvae | Filter paper/ maize seed | RT | C | A | C | C | A | C | C | C |
| *Musca domestica* (houseflies) | adults | Cotton wool/ sucrose | CT | A | C | B | — | — | — | — | C |
| *Blatella germanica* (cockroaches) | adults | Filter paper | RT | C | C | C | C | A | C | C | C |

In the Table it can be seen that the compounds exhibit useful insecticidal and acaricidal activity against a number of test species representing a wide variety of insect and acarine pests of economic importance.

What is claimed is:

1. A compound of formula:

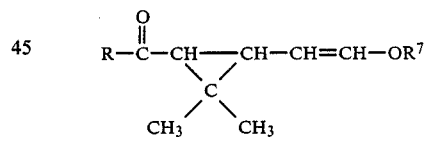

wherein R is alkoxy of up to 6 carbon atoms and $R^7$ is alkyl of up to 6 carbon atoms.

2. A compound of formula:

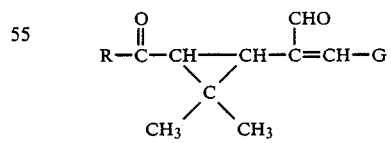

wherein G is either $OR^7$ where $R^7$ is alkyl of up to 6 carbon atoms or dimethylamino and R is alkoxy of up to 6 carbon atoms.

* * * * *

UNITED STATES PATENT AND TRADEMARK OFFICE
CERTIFICATE OF CORRECTION

PATENT NO. : 4,898,968

DATED : Feb. 6, 1990

INVENTOR(S) : Edward MCDONALD, Roger SALMON

It is certified that error appears in the above-identified patent and that said Letters Patent is hereby corrected as shown below:

ON THE TITLE PAGE:

Change "[62] Division of Ser. No. 928,461, Nov. 10, 1986, Pat. No. 4,760,443, which is a division of Ser. No. 712,252, Mar. 15, 1985, Pat. No. 4,661,488." to --[62] Division of Ser. No. 928,461, Nov. 10, 1986, Pat. No. 4,760,143, which is a division of Ser. No. 712,252, Mar. 15, 1985, Pat. No. 4,661,488.--

Signed and Sealed this

Twentieth Day of April, 1993

Attest:

MICHAEL K. KIRK

Attesting Officer

Acting Commissioner of Patents and Trademarks